United States Statutory Invention Registration [19]

[11] Reg. Number: H938

Paalman et al. [43] Published: Jul. 2, 1991

[54] REMOVAL OF HYDROXIDE ION FROM ALKOXIDE ION SOLUTIONS

[76] Inventors: H. Hunter Paalman, 240 Paloma Corte, Walnut Creek, Calif. 94598; Jonathan A. Okorley, 1608 Norine Dr., Pittsburg, Calif. 94565; James A. Sinclair, 4010 Old Pine Trail, Midland, Mich. 48640

[21] Appl. No.: 429,521

[22] Filed: Oct. 30, 1989

[51] Int. Cl.[5] ..... C07D 487/00; C07C 31/30

[52] U.S. Cl. ..... 544/263; 568/851

[58] Field of Search ..... 568/851; 544/263

[56] References Cited

U.S. PATENT DOCUMENTS

| | | | |
|---|---|---|---|
| 2,265,949 | 12/1941 | Loder et al. | 568/851 |
| 2,543,399 | 2/1951 | Calingaert | 568/851 |
| 3,644,602 | 2/1972 | Orwoll | 568/851 |
| 4,421,936 | 12/1983 | Smith et al. | 568/851 |
| 4,577,045 | 3/1986 | Matthes et al. | 568/851 |
| 4,584,414 | 4/1986 | Pruckmayr | 568/617 |
| 4,734,123 | 3/1989 | Monte et al. | 544/263 |
| 4,755,212 | 7/1988 | Keschick et al. | 544/263 |
| 4,818,273 | 4/1989 | Kleschick et al. | 544/263 |
| 4,857,665 | 8/1989 | Hinrichs et al. | 568/851 |
| 4,895,989 | 1/1990 | Sander et al. | 568/851 |

FOREIGN PATENT DOCUMENTS

| | | | |
|---|---|---|---|
| 37-11808 | 9/1938 | Japan | 568/851 |

*Primary Examiner*—John S. Maples
*Assistant Examiner*—Shean C. Wu

[57] ABSTRACT

The concentration of alkali metal hydroxide contaminants in solutions of alkali metal alkoxides in alcohols is reduced to below about 0.1 percent by adding an alkyl alkanoate ester. For example, a solution of sodium methoxide in methanol containing about 0.04 percent sodium hydroxide was obtained by adding a small amount of methyl acetate. The alkali metal alkanoate salt formed as a by-product does not deleteriously affect most uses of such solutions.

5 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

REMOVAL OF HYDROXIDE ION FROM ALKOXIDE ION SOLUTIONS

BACKGROUND OF THE INVENTION

The present invention relates to a process for removing the alkali metal hydroxide contaminants from alkali metal alkoxide in alcohol solutions by treatment with carboxylic acid esters.

Solutions containing alkali metal alkoxides and the corresponding alcohols are almost always contaminated with varying amounts of alkali metal hydroxides. These contaminants are generally formed as by-products in the preparation of alkali metal alkoxide solutions due to the presence of water in the alcohol employed and are additionally formed during the storage and handling of such solutions as a result of their absorption of water. Contamination of alkali metal alkoxide solutions by alkali metal hydroxides is, however, an important problem in that these contaminants reduce the yield of products prepared in processes using the solutions as a reagent and cause the formation of by-products which must be removed. The result is a higher cost of production and additional waste that must be disposed of.

There is currently no good way to remove alkali metal hydroxide contaminants from solutions containing alkali metal alkoxides and the corresponding alcohol. The general approach to the problem has been to try to avoid their formation in the preparation, storage, and use of such solutions.

SUMMARY OF THE INVENTION

It has now been found that small amounts of alkali metal hydroxides can be removed from solutions containing an alkali metal alkoxide and its corresponding alcohol by adding a small amount of an alkyl ester of an alkanoic acid to the solution and allowing the solution to stand for a period.

The present invention includes a process which comprises removing an alkali metal hydroxide from a solution containing an alkali metal alkoxide of the formula $$R—OM$$

wherein

M represents sodium, potassium, or lithium; and

R represents primary or secondary $C_1$–$C_8$ alkyl and its corresponding alcohol by adding an ester of the formula $$R'—CO_2—R''$$

wherein

R′ represents $C_1$–$C_3$ alkyl; and

R″ represents primary or secondary $C_1$–$C_8$ alkyl in an amount at least about equimolar with the amount of alkali metal hydroxide present and retaining the resulting mixture for a period of time at least sufficient for a portion of the alkali metal hydroxide to react with the ester and effectively remove at least a portion of the alkali metal hydroxide from the solution.

It is generally preferred to employ an ester wherein the alkyl moiety R″ of the ester is the same as the alkyl moiety R of the alkali metal alkoxide so as not to add another contaminant to the solution. Acetate esters are, further, often preferred.

The process is especially valuable for removing alkali metal hydroxide contaminants from alkali metal primary and secondary $C_1$–$C_4$ alkoxides and particularly valuable for removing such contaminants from alkali metal methoxides and ethoxides.

The invention further includes a solution comprising an alkali metal alkoxide of the formula $$R—OM$$

wherein

M represents sodium, potassium, or lithium; and

R represents primary or secondary $C_1$–$C_8$ alkyl and its corresponding alcohol and less than about 0.1 percent alkali metal hydroxide which solution was prepared by adding to a starting solution comprising a said alkali metal alkoxide and its corresponding alcohol and an alkali metal hydroxide an ester of the formula $$R'—CO_2—R''$$

wherein

R′ represents $C_1$–$C_3$ alkyl; and

R″ represents primary or secondary $C_1$–$C_8$ alkyl in an amount at least about equimolar with the amount of alkali metal hydroxide present in the starting solution and retaining the resulting mixture for a period of time at least sufficient for a portion of the alkali metal hydroxide to react with the ester and effectively remove at least a portion of the alkali metal hydroxide.

DETAILED DESCRIPTION OF THE INVENTION

In the process of the present invention the alkali metal hydroxide contaminants of solutions containing an alkali metal alkoxide and the corresponding alcohol are reduced in concentration to acceptable levels by means of their reaction with alkyl esters of alkanoic acids. The solution then becomes contaminated merely with an alkali metal salt of an alkanoic acid and, in some instances, an alcohol, neither of which is deleterious to most applications of alkali metal alkoxide in alcohol solutions. The reaction involved can be illustrated as follows $$MOH + R'—CO_2—R'' \rightarrow R''OH + R'—CO_2M$$

wherein M, R, R′, and R″ are as defined in the Summary of the Invention.

The solutions containing an alkali metal alkoxide and the corresponding alcohol that are employed in the present invention include those wherein the alcohol contained is a primary or secondary alcohol having 1 to 8 carbon atoms. Such alcohols include methanol, ethanol, 1-methylethanol, butanol, 2-methylpropanol, 1-methylheptanol, 2,2-dimethylpropanol, and the like. The process is most often utilized to remove alkali metal hydroxides from alkali metal alkoxide solutions derived from primary and secondary $C_1$–$C_4$ alcohols. It is especially useful for removing alkali metal hydroxides from alkali metal methoxide and ethoxide solutions. The alkali metals involved includes sodium, potassium, and lithium.

The solutions containing alkali metal alkoxides and the corresponding alcohol can contain other substances, such as other alkali metal salts, compatible solvents, and other compatible organic compounds. Compatible solvents and other organic compounds are those that, in the amount present, do not cause the alkali metal to precipitate, do not react with the alkali metal to alkoxide or the alcohol in a significant way over the period that the solution is held, and do not interfere with the intended use to be made of the solution. Compatible solvents include hydrocarbons such as benzene, toluene, and hexane, ethers such as diethyl ether, tetrahydrofuran, dioxane, and dimethoxyethane, N,N-dialkylamides such as N,N-dimethylformamide and N-methyl-2-pyrrolidinone, dimethyl sulfoxide, and the like.

The alkali metal hydroxide contaminants present in the subject solutions include sodium, potassium, and lithium hydroxides. It is assumed for the purposes of this application that all of the water present in the subject solutions is present in the form of an alkali metal hydroxide. In reality, a finite amount of water is present due to the existence of the following equilibrium.

$$HOM + ROH \rightleftharpoons ROM + HOH$$

Nearly all of the water, however, is actually in the form of an alkali metal hydroxide and all of it reacts as if it were in the form of an alkali metal hydroxide.

The solutions containing alkali metal alkoxides and the corresponding alcohol to be treated in the process generally contain at least one such alkali metal hydroxide in an amount of at lest about 0.05 percent. The upper limit of concentration is not important and is usually limited only by the solubility of the compound in the medium and the amount of by-products from the present process that can be tolerated in the decontaminated solution, which amount will depend on the use to be made of the solutions. The alkali metal hydroxides are, however, usually present to the extent of less than about 5 percent. Solutions contaminated with less than about 2 percent are typically employed.

The esters employed in the invention are generally alkyl esters of alkanoic acids that readily react with alkali metal hydroxides at typical ambient temperatures. Suitable esters include esters of the formula $$R'—CO_2—R''$$

wherein R' represents $C_1$–$C_3$ alkyl and R'' represents a primary or secondary $C_1$–$C_8$ alkyl group.

It is generally preferred to employ an ester wherein the group R'' is the same as the group R of the alcohol and the alkali metal alkoxide. This selection allows one to remove the alkali metal hydroxide present in a solution without introducing a new alcohol contaminant. It is further preferred to employ an ester wherein R'' represents a primary or secondary $C_1$–$C_4$ alkyl group. Methyl and ethyl esters are especially preferred. It is further preferred to employ an ester wherein R' represents methyl; i.e., acetate esters. Acetate esters are relatively inexpensive and react relatively rapidly with alkali metal hydroxides. Methyl and ethyl acetates are specifically preferred esters.

The amount of ester to be employed will vary depending on the amount of alkali metal hydroxide present in the solution and the effect. If any, of excess ester on the alkali metal alkoxide solution obtained. Generally, the more ester employed the faster the reaction of the process will proceed and the more completely the alkali metal hydroxide will be removed. On the other hand, large excesses may interfere with the intended use of the solution and add to the cost. Generally about an equimolar amount of ester compared with the alkali metal hydroxide present is sufficient to give a significant reduction in alkali metal hydroxide contamination. It is preferred to use an excess of about 3 to about 200 percent. Excesses of about 5 to about 100 percent are sometimes more preferred.

The process of the present invention is conducted combining an alkali metal hydroxide contaminated solution containing an alkali metal alkoxide and the corresponding alcohol with an alkyl ester of an alkanoic acid and following the mixture to react. The contacting can be done in any known way. It is generally most suitable to add the ester to the contaminated solution. Usually some sort of agitation is provided to ensure the complete mixing of the reagents and protection from adventitious moisture is provided to prevent further contamination. The process can be conducted on either a batch or a continuous basis.

The mixture can be retained for reaction an any temperature between the freezing point and the boiling point of the mixture. It is typically retained at about 0° C. to about 100° C. and often retained at about 20° C. to about 80° C. It is usually most convenient to conduct the process at ambient temperature or at the temperature the solution being decontaminated will be subsequently used.

The mixture is retained for reaction until a significant amount of the alkali metal hydroxide has reacted with the ester and is, in this way, removed from the solution. Reaction times of about 10 minutes to about 24 hours are typical. The reaction time depends partially on the ester employed and the temperature at which the process is conducted. Generally, the lower molecular weight the ester and the higher the temperature, the shorter the time required. Further, the more time allotted, the more completely the alkali metal hydroxide will be removed.

Application of the process of the present invention typically reduces the concentration of alkali metal hydroxide in a solution containing an alkali metal alkoxide and its corresponding alcohol to below about 0.10 percent (1000 parts per million). It is sometimes preferred to utilize conditions under which concentrations below about 0.05 percent (500 parts per million) are achieved and often more preferred to utilize conditions under which concentrations below about 0.01 percent (100 parts per million) are achieved.

The solutions containing an alkali metal alkoxide and its corresponding alcohol that are obtained as a result of the present invention are suitable for many applications, including as a reagent for the preparation of organic substances. This is particularly the case where the chemical substances are prepared by processes wherein the presence of an alkali metal hydroxide in the solution significantly reduces yield or produces a by-product that engenders the need for additional purification. Typical reactions of this sort include displacement reactions of alkoxides on organic halides, such as bromalkanes, chloropyridines, activated fluorobenzenes, acyl chlorides, sulfonyl chlorides, and the like, to produce dialkyl ethers, alkoxypyridines, alkoxybenzenes, alkyl esters of alkanoic acids, alkyl esters of sulfonic acids, and the like, respectively. Other typical reactions of the type include cyclization reactions of, for example, malonic acid esters and acetoacetic acid esters wherein the alkoxide is a catalyst or a combination catalyst and reactant.

A reaction in the latter category is the cyclization of a 3-amino-5-(N-(substituted-phenyl)aminosulfonyl)-1,2,4-triazole with a dialkyl malonate ester to obtain a 5,7-dihydroxy-N-(substituted-phenyl)-1,2,4-triazolo[1,5-a]pyrimidine-2-sulfonamide in the presence of an alkali metal alkoxide, which is described in U.S. Pat. No. 4,818,273. Low yields were reported. Yields above 80 percent, however, are achievable when the process of the present invention is employed to remove alkali metal hydroxides. For example, yields of about 80 percent are obtained when the reagents employed are dimethyl malonate, ethanol, sodium methoxide in methanol, and 3-amino-5-(N-2,6-dichloro-3-methylphenylaminosulfonyl)-1,2,4-triazole and the system is treated with ethyl acetate to remove sodium hydroxide before the addition of the dimethyl malonate.

The following examples are presented to illustrate the invention and should not be construed as limiting.

EXAMPLES

EXAMPLE 1

Removal of Sodium Hydroxide from Sodium Methoxide in Methanol with Methyl Acetate A 2791 grams (g) sample of 25 percent solution of sodium methoxide in methanol was analyzed and found to contain 0.36±0.05 percent sodium hydroxide (10.1 g, 0.25 mol). To this was added 20.5 g (0.28 mol) of methyl acetate. The reagents were mixed and the mixture was allowed to stand at ambient temperature overnight. The solution was reanalyzed and found to contain 0.05 percent sodium hydroxide. Analyses were done by Karl Fischer titration using an automatic coulometric titrator to generate the Karl Fischer reagent and conduct the titration. Benzoic acid was added to the cell electrolyte before titration as a buffering agent.

Similarly, to an 18.1 kilogram sample of a 25 percent solution of sodium methoxide in methanol found to contain 0.42±0.02 percent sodium hydroxide (76.0 g, 1.90 mol) was added 141 g (1.90 mol) of methyl acetate. The reagents were mixed and the mixture was allowed to stand by ambient temperature overnight. The solution was reanalyzed and found to contain 0.04 percent sodium hydroxide.

EXAMPLE 2

Removal of Sodium Hydroxide from Sodium Methoxide in Methanol with Ethyl Acetate A 37.7 g sample of a 25 percent solution of sodium methoxide in methanol was analyzed and found to contain 0.48 percent sodium hydroxide (0.0181 g, 0.0045 mol). To 37.5 g of this was added 0.46 g (0.0052 mol) of ethyl acetate. The reagents were mixed and the mixture was allowed to stand at ambient temperature. The solution was reanalyzed after 1 hour and 16 hours and found to contain 0.13 and 0.06 percent sodium hydroxide, respectively. Analyses were done as in Example 1.

Similarly, a mixture containing 23.8 g of 25 percent sodium methoxide in methanol, 14.3 g of propanol, and 4.7 g of 3-amino-5-N-(2,6-dichloro-3-methylphenylsulfonylamino)-1,2,4-triazole was analyzed as in Example 1 and found to contain 0.71 percent sodium hydroxide (0.30 g, 0.0075 mol). To a 42.4 g portion of this was added with stirring 0.73 g (0.0083 mol) of ethyl acetate. The mixture was allowed to react at 27°–30° C. and was analyzed as in Example 1 at intervals. After 1 hour, 2.25 hours, 4.2 hours, and 21 hours the sodium hydroxide concentration was 0.19, 0.13, 0.079, and 0.061 percent, respectively. Another 0.16 g (0.0018 mol) of ethyl acetate was added and after 4.5 hours the solution was analyzed and found to contain 0.033 percent sodium hydroxide.

EXAMPLE 3

Removal of Sodium Hydroxide from Sodium Butoxide in Butanol with Butyl Propionate and with Methyl Acetate An 18.0 g sample of a 20 percent solution of sodium butoxide in butanol was analyzed was found to contain 1.28 percent sodium hydroxide (0.231 g, 5.77 mmol). To 18.08 g of this solution was added 1.094 g (8.42 mmol) of butyl propionate. The reagents were mixed and the mixture was allowed to stand at ambient temperature for 1.2 hours. It was then reanalyzed and found to contain 101 ppm (0.010 percent) sodium hydroxide. Analyses were done as in Example 1.

In the same manner 0.796 g (10.76 mmol) of methyl acetate was added to 18.52 g of the solution and the mixture was allowed to stand at ambient temperature for 1 hour. The solution was then reanalyzed and found to contain 271 ppm (0.027 percent) sodium hydroxide.

EXAMPLE 4

Preparation of 5,7-Dihydroxy-N-(2,6-dichloro-3-methylphenyl)-1,2,4-triazolo[1,5-a]pyrimidine-2-sulfonamide Using Sodium Ethoxide Purified with Ethyl Acetate A mixture of 17.8 g (0.20 mol) of ethyl acetate and 600 milliliters (ml) of ethanol containing about 0.01 percent water was prepared in a 3-necked flask equipped with a stirrer, a Dean-Starks trap and condenser, a thermometer well, a dropping funnel, and a heating mantle and to this was added slowly with stirring 445 g of sodium methoxide in methanol containing about 0.3 percent sodium hydroxide. The mixture was heated to reflux with stirring and about 400 g of volatiles was removed by distillation at which time the pot temperature was 89° C. The mixture remaining in the flask was found to contain about 1.0 percent (0.17 mole) of sodium hydroxide by analysis. 3-Amino-5-N-(2,6-dichloro-3-methylphenylaminosulfonyl)-1,2,4-triazole (134.3 g of 90.1 percent assay, 0.38 mol) containing about 0.45 percent water was added. There was a slight exotherm. The mixture was stirred for about 15 hours and was then warmed to about 45° C. Diethyl malonate (132.9 g, 0.83 mol) was then added slowly. The temperature was increased to about 76° C. partly as a result of an exotherm and partly with heat. After about 20 hours the mixture was allowed to cool and the sodium salt of the desired product was removed by filtration. This was extracted with the mixture of alcohols taken as distillate above. The wet cake remaining amounted to 408 g and was found to be about 50 percent volatiles. This material was analyzed by high pressure liquid chromatography and found to contain 0.30 mole of the trisodium salt of the title compound, 0.041 mole of unreacted 3-amino-5-N-(2,6-dichloro-3-methylphenylaminosulfonyl)-1,2,4-triazole, and 0.023 mole an uncyclized by-product. This amounts to a yield of 88 percent of theory. The loss to uncyclized by-product amounted to 7 percent of theory. A 206 g portion of the wet cake was dissolved in 400 ml of cold water (about 3° C.) and 69.96 ml of concentrated hydrochloric acid was added slowly with cooling at about 0°–10° C. The final pH was 1.2. The resulting solid was recovered by filtration, extracted with about 600 ml of ice cold water and dried to obtain the title compound as a white solid.

What is claimed is:

1. A process which consists essentially of removing an alkali metal hydroxide from a solution containing essentially an alkali metal alkoxide of the formula $$R—OM$$

wherein

M represents sodium, potassium, or lithium; and

R represents primary or secondary $C_1$–$C_8$ alkyl and its corresponding alcohol by adding an ester of the formula $$R'—CO_2—R''$$

wherein

R′ represents $C_1$–$C_3$ alkyl; and

R″ represents primary or secondary $C_1$–$C_8$ alkyl in an amount at least about equimolar with the amount of alkali metal hydroxide present and retaining the resulting mixture with protection from adventitious moisture for a period of time at least sufficient for a portion of the alkali metal hydroxide to react with the ester and effectively remove at least a portion of the alkali metal hydroxide from the solution.

2. A process according to claim 1 wherein R and R″ each independently represent primary or secondary $C_1$–$C_4$ alkyl.

3. A process according to claim 2 wherein R and R″ each independently represent methyl or ethyl.

4. A process according to claim 1 wherein R′ represents methyl.

5. A process according to claim 4 wherein the ester is methyl or ethyl acetate.

* * * * *